United States Patent [19]

Wu et al.

[11] 4,191,715

[45] Mar. 4, 1980

[54] FLAME RETARDING COMPOUND

[75] Inventors: Chester C. Wu, Raleigh, N.C.; Albert Y. Garner, Yellow Springs, Ohio

[73] Assignee: Monsanto Company, St. Louis, Mo.

[21] Appl. No.: 921,649

[22] Filed: Jul. 3, 1978

[51] Int. Cl.² ............................................. C07F 9/06
[52] U.S. Cl. ........................... 260/927 N; 528/168; 528/169; 528/287; 252/8.1
[58] Field of Search ................................... 260/927 N

[56] References Cited

U.S. PATENT DOCUMENTS

| | | | |
|---|---|---|---|
| 3,462,518 | 8/1967 | Kober et al. | 260/297 N |
| 4,029,634 | 6/1977 | Meredith | 260/927 N |
| 4,094,856 | 6/1978 | Guschl | 260/927 N |

*Primary Examiner*—Mary C. Lee

*Attorney, Agent, or Firm*—Robert L. Broad, Jr.

[57] ABSTRACT

A compound having the formula

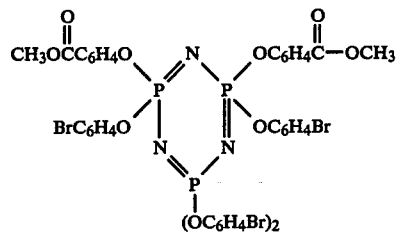

This compound is useful in enhancing the flame retardancy of polyesters.

1 Claim, No Drawings

FLAME RETARDING COMPOUND

BACKGROUND OF THE INVENTION a. Field of the Invention

This invention relates to compounds having flame retarding characteristics.

b. Description of the Prior Art

The use of flame retarding additives in polyester fibers is known. Strict requirements must be met in a flame retardant which is to be used as an additive for polyester fibers and most compounds which are known to have flame retarding characteristics are, for one reason or another, unsuitable for such use. In addition to conferring flame retardancy on the fiber, the additive must also not have any deleterious effects on the fiber. Additives which will leach out of the fiber during dyeing or washing are unsuitable. Additives which affect the color of the fibers or adversely affect physical properties of the fibers are undesirable.

The flame retarding additives of the present invention significantly enhance the flame retardancy of polyester fibers without having any significant adverse effect on these fibers.

SUMMARY OF THE INVENTION

A compound having the formula

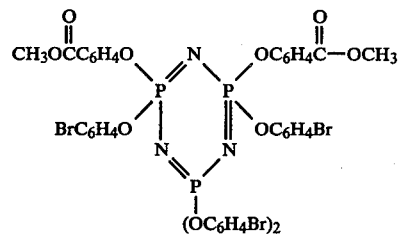

This compound is useful as a flame retardant in polyesters. Flame retardancy is significantly improved without significant adverse effects on fibers made from the polyesters.

DETAILED DESCRIPTION OF THE INVENTION

The compound of the present invention has the formula

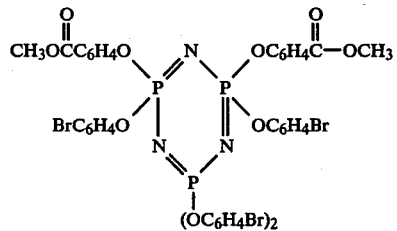

Preparation of Tetrakis(4-bromophenoxy)-bis (4-carbomethoxyphenoxy) cyclotriphosphazene

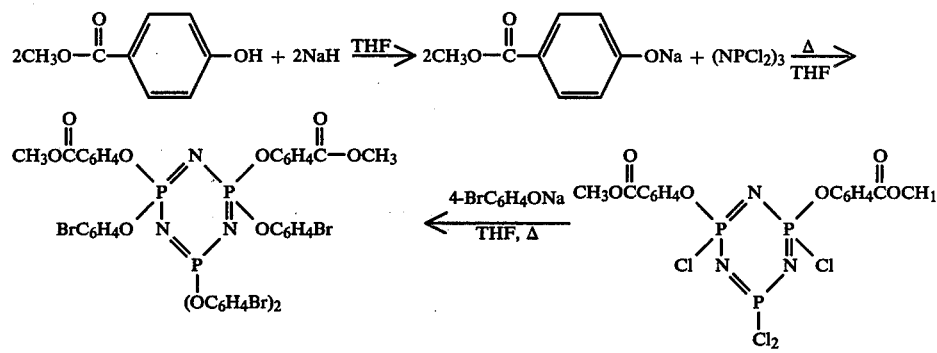

A solution of 30.8 g (0.2 m) of methyl-4-hydroxybenzoate in 100 ml of tetrahydrofuran (THF) was added dropwise with stirring to a slurry of sodium hydride that had been obtained by rinsing 9.6 g (0.2 m) of a 50% oil dispersion with benzene followed by the addition of 200 ml of THF. When the entire ester solution had been added, the mixture was stirred for an additional half-hour. A solution of 34.8 g (0.1 m) of (NPCl$_2$)$_3$ in 100 ml of THF was added rapidly with stirring. The reaction mixture became warm. This mixture was heated to reflux and was kept there for 23 hours.

A slurry of sodium 4-bromophenol prepared from 76.12 g (0.44 m) of the phenol and 10.12 g (0.44 m) of sodium metal in 400 ml of THF was added to the refluxing mixture. This new mixture was refluxed for 115 hours.

Upon cooling, the insolubles were filtered from the reaction mixture, leaving a clear filtrate. Removal of the solvent on a rotary evaporator left 115.7 g of a crude syrup. This material was dissolved in 300 ml of benzene and was washed three times with 100 ml of 5 percent sodium hydroxide and then with 100 ml of water. After drying over anhydrous magnesium sulfate, the solution was filtered and the benzene was removed on a rotary evaporator using a 65° C. water bath. The resultant light amber syrup became thicker and opaque upon cooling and had a weight of 86.7 g. The sample was chilled in dry ice and crushed to remove it from the flask. Upon warming to room temperature, the material became syrupy again. The sample was heated under a vacuum at 80° C. to remove traces of solvent. An x-ray florescence spectrum showed the syrup to contain 2.1 percent chlorine.

The sample in 100 ml of THF was added to a slurry of sodium 4-bromophenolate from 51.9 g (0.3 m) of the phenol and 6.9 g (0.3 m) of sodium metal and 300 ml of THF. This mixture was refluxed for 43 hours and then cooled and filtered. The filtrate was concentrated under vacuum leaving a red syrup. The syrup was dissolved in 150 ml of benzene and was washed twice with 50 ml of 5 percent sodium hydroxide then with 100 ml of water. After drying over anhydrous magnesium sulfate, a pale yellow solution was left after filtration. Removal of the solvent on a rotary evaporator yielded a tan semi-solid having a weight of 53.3 g. The solid was chilled in dry ice and crushed. Upon warming to room temperature it did not become soft and tacky. This material was dried overnight at 80° C. in a vacuum oven to remove occluded residual solvents, leaving a weight of 52.6 g.

The IR spectrum corresponded to that of a small sample made previously. An x-ray florescence showed 0.1 percent chlorine.

Proton nuclear magnetic resonance ('H NMR) analysis:

|  | Theory | Found |
|---|---|---|
| H-C(=O)-C- (with two H) | 4.0 | 4.0 |
| aromatic | 24.0 | 24.0 |
| OCH3 | 6.0 | 5.7 |

Anal. Calc'd. for C40H30Br4N3O10P3:

| C | H | Br | N | P | Cl |
|---|---|---|---|---|---|
| 42.70 | 2.69 | 28.41 | 3.73 | 8.26 | 0.00 |

Found:

| 43.95 | 2.97 | 26.92 | 3.51 | 8.29 | 0.34 |

Molecular weight: Calc'd: 1097 - Found: 1075 (in benzene)

The effectiveness of these flame retarding compounds was determined by incorporating them in polyester fibers and then testing the fiber.

FIBER FORMATION

The prepolymer used to prepare the polymers of this invention was prepared as follows:

A slurry consisting of an antimony catalyst, ethylene glycol and terephthalic acid in the molar ratio of 2/1 was reacted at 270° C. and 20 pounds pressure in a continuous polyester esterifier. Water of reaction and some ethylene glycol were removed by distillation and the low molecular weight prepolymer product collected continuously through a valve at the bottom of the reactor. The rate of removal of prepolymer was such as to maintain a constant level in the reactor and the average residence time in the reactor was 135 minutes. The low molecular weight prepolymer collected had an intrinsic viscosity of 0.08 and carboxyl concentration of 616 μeq/g both measured in the usual way.

The flame retardant polymer and filaments were prepared as follows:

Two hundred grams of the prepolymer was added to a 0.9-liter capacity, stirred, batch autoclave, purged with nitrogen and heated to 270° C. Premelted tetrakis (4-bromophenoxy) bis (4-carbomethoxyphenoxy) cyclotriphosphazene, 16.9 grams, having the structure shown above was added to the prepolymer through an addition port atop the autoclave. Pressure in the system was reduced by applying a vacuum and polymerization to form a high molecular weight random copolymer continued at temperature of 275° C. and pressures of less than 2 mm Hg until the desired molecular weight was obtained. A polymer with an intrinsic viscosity of 0.54 was obtained in a period of 82 minutes from the beginning of pressure reduction.

Inasmuch as this flame retarding compound has terminal reactive groups, it can react with the prepolymer to become an integral part of the polymer chain under polymerization conditions. However, we do not know to what extent this occurs in the polymer forming steps described herein. The extent of copolymerization is not of real importance, since the flame retardancy of the polymer is not changed by copolymerization or lack of it.

The polymer was extruded through a ten hold spinneret, the filaments quenched in a water batch and collected on a Leesona model 955 take-up machine. The ten filaments were drawn 5.0 times over a 80° C. hot pin to yield a 57 total denier filament. This drawn filament had good whiteness with a purity value of 3.5 and a brightness of 93.02 as determined from tristimulus values obtained with a G.E. Recording Spectrophotometer. The copolymer filaments analyzed 0.62% phosphorus and 1.92% bromine, melted at 252° C. and the Instron single filament breaks showed a breaking elongation of 23.5%. The copolymer filament also showed good UV light stability and good dyed lightfastness.

FLAME RETARDANCY TEST

The flame retardancy of polymers including the flame retarding compounds of this invention were determined by knitting the yarn prepared as described above into a 9 centimeter diameter tubing with 1 ply of 50 denier fiberglass on a Lawson knitter to contain 14 courses per cm with a 54 gauge head of 220 needles. Oxygen indices of the knit tubing, containing about equal weights of polyester yarn and fiberglass, were determined using an MKM Model JD-14 oxygen index (OI) flammability tester. Knit tubing was mounted on a 4.4×15.2 cm metal frame and oxygen indices determined with a flow rate of 4±1 cc/second combined oxygen and nitrogen.

A copolymer prepared as described above with 8.5 weight % of the flame retardant of this invention had an oxygen index of 22.6 units. Unmodified poly(ethylene terephthalate) under the same conditions had an oxygen index of 19.8. The ΔOI was 2.8 units. Fiber properties were good. The ΔOI was determined as a difference in OI between the polymers containing the flame retardants of this invention and unmodified poly(ethylene terephthalate).

Another polymer was formed as described above to contain 5.5 weight percent of the flame retarding compound. Fibers from this polymer tested as described above had an OI of 21.6 which the same polyester, containing no flame retardants, had an OI of 19.9. The ΔOI was 1.7. Fiber properties were good.

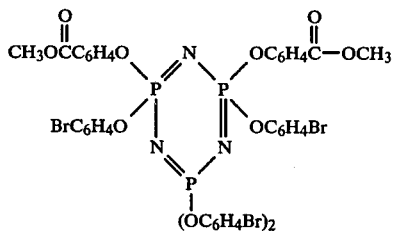

What is claimed is:

1. A flame retarding agent having the formula: